United States Patent [19]

Smith, Jr.

[11] 4,256,755
[45] Mar. 17, 1981

[54] METHOD OF USING N-SUBSTITUTED DIHYDRO-2-OXAZOLAMINES AS ANALGESICS

[75] Inventor: Dewey H. Smith, Jr., Wilmington, Del.

[73] Assignee: E. I. Du Pont de Nemours & Company, Wilmington, Del.

[21] Appl. No.: 144,543

[22] Filed: Apr. 28, 1980

[51] Int. Cl.$^3$ .............................................. A61K 31/42
[52] U.S. Cl. .................................................... 424/272
[58] Field of Search ......................................... 424/272

[56] References Cited

U.S. PATENT DOCUMENTS

| | | | |
|---|---|---|---|
| 2,027,031 | 1/1936 | Engelmann | 260/44 |
| 2,811,529 | 10/1957 | Bloom | 260/307 |
| 2,870,159 | 1/1959 | Bloom | 260/307 |
| 2,870,161 | 1/1959 | Bloom | 260/307 |
| 2,883,410 | 4/1959 | Bloom | 260/456 |
| 2,889,351 | 6/1959 | Bloom | 260/456 |
| 3,432,600 | 3/1969 | Harvey, Jr. | 424/272 |
| 3,499,084 | 3/1970 | Levitt | 424/272 |
| 3,598,833 | 8/1971 | Hiltmann et al. | 260/307 |

FOREIGN PATENT DOCUMENTS

| | | |
|---|---|---|
| 1132409 | 10/1968 | United Kingdom . |
| 1138530 | 1/1969 | United Kingdom . |
| 1139458 | 1/1969 | United Kingdom . |

OTHER PUBLICATIONS

Chem. Abst. 55–6470b (1961).
Chem. Abst. 76–99639u (1972).

*Primary Examiner*—Stanley J. Friedman

[57] ABSTRACT

Certain N-substituted dihydro-2-oxazolamines are useful as analgesics.

5 Claims, No Drawings

METHOD OF USING N-SUBSTITUTED DIHYDRO-2-OXAZOLAMINES AS ANALGESICS

BACKGROUND OF THE INVENTION

This invention relates to the use of certain N-substituted 2-oxazolamines as analgesics.

There is a well-defined need for compounds which have potent analgesic activity, which are non-addictive and which are relatively free of side effects. Presently available non-narcotic analgesics, for example, aspirin, are limited in the degree of pain which they can suppress. The narcotic analgesics tend to be addictive and suffer a high degree of abuse liability. Use of narcotic analgesics is also often accompanied by undesirable side effects, including depression of respiration, constipation, sedation, euphoria, dysphoria, excitation, dizziness, nausea, vomiting, weakness, palpitation, sweating, visual disturbances and dry mouth. Still another undesirable feature of the narcotic analgesics is the high degree of tolerance which they demonstrate.

The N-substituted 2-oxazolamines disclosed herein are generally known in the art. They are variously described as having antihypertensive, central nervous depressant, tranquilizing, anesthetic, sedative, vasoconstrictive and blood pressure depressant activity. Although a few of the compounds are disclosed as being useful for potentiating the effects of analgesics, none of them have been disclosed to be useful alone as analgesics.

SUMMARY OF THE INVENTION

It has now unexpectedly been discovered that N-substituted 2-oxazolamines of Formula I have useful analgesic activity.

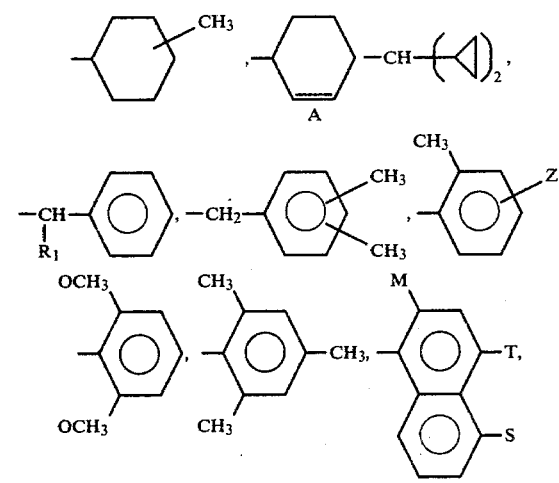

where R is

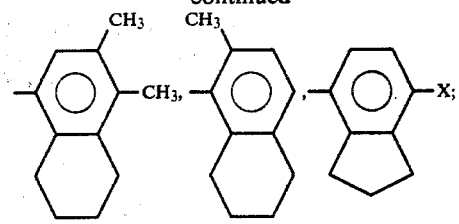

A is —CH=CH—CH=CH— or —S—CH=CH;
$R_1$ is $CH_3$ or

Z is H, $CH_3$, $OCH_3$ or Cl;
S and T are both H or may be taken together to be —$CH_2CH_2$—; and
M and X are independently H or $CH_3$; and pharmaceutically suitable acid addition salts thereof. These compounds are characterized by rapid onset of action, high oral potency, long duration of action and the ability to alleviate deep-seated pain. Abuse liability is expected to be low or non-existent.

The following compounds are specifically preferred due to their high analgesic activity:
4,5-dihydro-N-(2-methylcyclohexyl)-2-oxazolamine
4,5-dihydro-N-(1,2,3,4-tetrahydro-1-naphthalenyl)-2-oxazolamine
4,5-dihydro-N-(1-phenylethyl)-2-oxazolamine.

More preferred for its high analgesic activity is the compound 4,5-dihydro-N-(4,5,6,7-tetrahydrobenzo [b] thiophen-4-yl)-2-oxazolamine.

DETAILED DESCRIPTION OF THE INVENTION Synthesis

The compounds used in the method of this invention may be prepared according to methods known in the art. One method involves reacting an isocyanate of the formula RNCO, where R is as defined above, with a β-substituted alkylamine, for example, β-chloroethylamine, followed by heating:

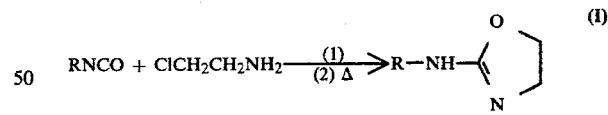

Alternatively, an amine of the formula $RNH_2$ may be reacted with a β-substituted alkylisocyanate, for example β-bromoethylisocyanate, followed by heating:

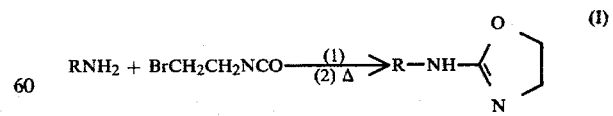

These methods are described in a number of publications, including U.S. Pat. No. 3,499,084; U.S. Pat. No. 2,889,351; U.S. Pat. No. 2,883,410; U.S. Pat. No. 2,870,161; U.S. Pat. No. 2,870,159; U.S. Pat. No. 2,881,529; U.S. Pat. No. 2,027,031; U.S. Pat. No. 3,432,600; and U.S. Pat. No. 3,626,067. The disclosures of these references are herein incorporated by reference.

Still another method for preparing these N-substituted 2-oxazolamines involves reacting an isocyanide dichloride of the formula R—N=CCl$_2$, where R is as defined above, with ethanolamine:

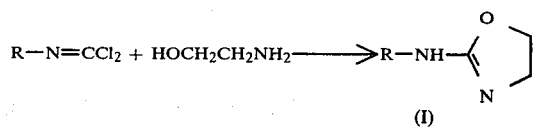

(I)

This method, too, is described in a number of publications, including British Pat. No. 1,139,458; U.S. Pat. No. 3,598,833; British Pat. No. 1,132,409; and British Pat. No. 1,138,530. These disclosures are herein incorporated by reference.

Pharmaceutically suitable acid addition salts of the compounds of this invention can be prepared by treatment of the free base with the appropriate acid, for example, hydrochloric or sulfuric acid.

UTILITY

The analgesic potency of the N-substituted oxazolamines is demonstrated by the phenylquinone writhing test, modified from Siegmund, E. et al., *Proc. Soc. Exptl. Biol. Med.*, 95, 729 (1957). Drug potency in this test correlates well with potency in man.

Mice injected intraperitoneally with phenyl-p-benzoquinone (phenylquinone) develop a characteristic writhing syndrome. This syndrome is prevented by all known analgesic drugs including aspirin, codeine, morphine, meperidine, nalorphine, pentazocine and d-propoxyphene.

The test compounds were dissolved or suspended in PVA-acacia (1% W/V polyvinyl alcohol [Elvanol ® 50-05], 5% W/V acacia, U.S.P. and 0.1% W/V methylparaben U.S.P. in distilled water) and injected into mice subcutaneously in the neck nape or were given orally by intubation. Fifteen or thirty minutes later, depending on time of peak action, 0.25 ml of 0.02% phenylquinone was given intraperitoneally. The mice were then watched for 10 minutes for the writhing syndrome. Failure to writhe even once during the 10-minute period constituted analgesia. The results are expressed in terms of ED$_{50}$, the dose at which half of the mice failed to writhe during the 10-minute observation period. These results are reported in Table I. It can be seen that the N-substituted 2-oxazolamine compounds are extremely potent analgesics. All of the tested compounds are at least six times more potent orally than the standard pentazocine and most of them are more potent than even the strong analgesic morphine.

TABLE I

R—NH—(oxazoline ring: N, O, CH$_2$CH$_2$)

| Compound R | Mouse Oral ED$_{50}$ Anti-PQW (mg/kg) | Compound R | Mouse Oral ED$_{50}$ Anti-PQW (mg/kg) |
|---|---|---|---|
| 4,5,6,7-tetrahydrobenzo[b]thien-3-yl | 0.04 | 5,6,7,8-tetrahydronaphthalen-1-yl with CH$_3$ | 5. |
| 5,6,7,8-tetrahydronaphthalen-1-yl | 0.1 | 5,6,7,8-tetrahydronaphthalen-1-yl with two CH$_3$ | 0.9 |
| 2-methylcyclohexyl | 0.6 | 2,6-dimethylphenyl | 0.97 |
| 2-methylphenyl | 1.4 | naphthalen-1-yl | 1.8 |

TABLE I-continued

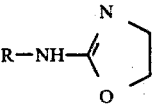

| Compound R | Mouse Oral ED$_{50}$ Anti-PQW (mg/kg) | Compound R | Mouse Oral ED$_{50}$ Anti-PQW (mg/kg) |
|---|---|---|---|
| 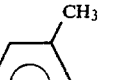 | 0.2 | 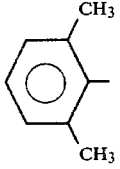 | 2.0 |
| 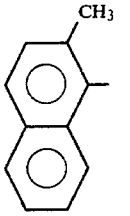 | 0.2 | 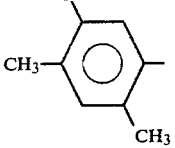 | 1.8 |
| 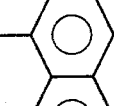 | 0.3 | 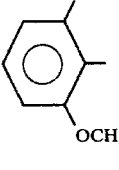 | 0.6 |
| 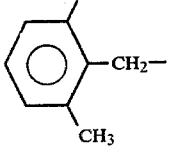 | 9.0 | 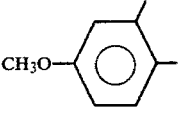 | 0.7 |
| 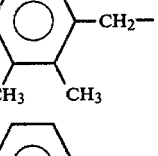 | 2.1 | 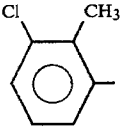 | 0.08 |
| 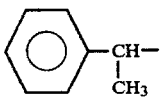 | 2.5 | 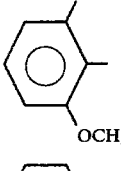 | 0.9 |
| 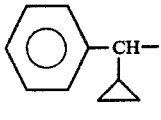 | 1.6 | 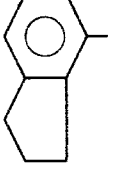 | 2.4 |
| 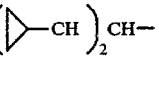 | 1.2 | morphine | 3.0 |
| | | pentazocine | 56. |

Naloxone, a potent narcotic antagonist with no analgesic properties, blocks analgesia (mouse phenylquinone test) of narcotics such as morphine but not of non-narcotics such as aspirin. The potency of naloxone in blocking analgesia correlates directly with human addiction liability of the analgesic.

The addiction liability of the compounds 4,5-dihydro-N-(4,5,6,7-tetrahydrobenzo[b]thiophen-4-yl)-2-oxazolamine was studied using the mouse phenylquinone writhing test described above. The subject compound was administered subcutaneously at the estimated $ED_{90}$, the dose at which 90% of the mice fail to writhe during the observation period. Simultaneously, naloxone was given subcutaneously in the groin in log-spaced doses. Mice were observed for writhing over a period of ten minutes at the times of peak analgesia. It was observed that the analgesic $ED_{50}$ of the subject compound was not altered by the simultaneously administered naloxone. The addiction liability of the compound is, therefore, expected to be low or even low-existent.

DOSAGE FORMS

The analgesic agents of this invention can be administered to alleviate pain in mammals by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health and weight of the recipient; nature and extent of symptoms, kind of concurrent treatment, frequency of treatment, and the effect desired. Usually a daily oral dosage of active ingredient can be about 0.001 to 10 milligrams per kilogram of body weight. Ordinarily, when the more potent compounds of this invention are used, 0.0025 to 2.0 and preferably 0.01 to 0.2 milligrams per kilogram per day, given in divided doses 2 to 4 times a day or in sustained release form, is effective to obtain desired results. These drugs may also be administered parenterally.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets and powders, or in liquid dosage forms, such as elixirs, syrups and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coating for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc and 6 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

What is claimed is:

1. A method of alleviating pain in a mammal comprising administering to a mammal having pain an effective analgesic amount of a compound of the formula

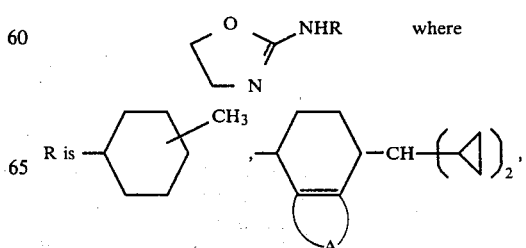

-continued

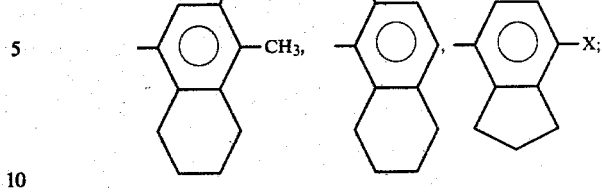

where
A is —CH=CH—CH=CH— or —S—CH=CH—;
$R_1$ is $CH_3$ or

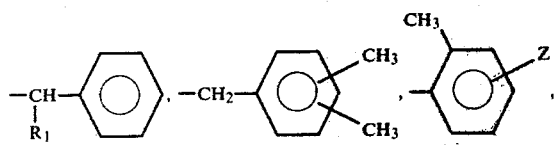

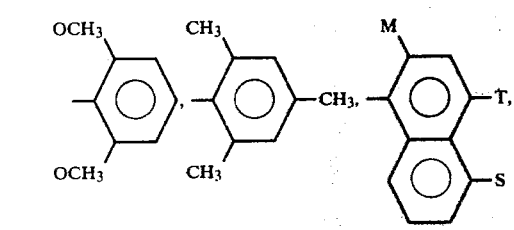

Z is H, $CH_3$, $OCH_3$ or Cl;
S and T are both H or may be taken together to be —$CH_2CH_2$—; and
M and X are independently H or $CH_3$; and pharmaceutically suitable acid addition salts thereof.

2. The method of claim 1 wherein the compound is 4,5-dihydro-N-(4,5,6,7-tetrahydrobenzo-[b]thiophen-4-yl)-2-oxazolamine.

3. The method of claim 1 wherein the compound is 4,5-dihydro-N-(2-methylcyclohexyl)-2-oxazolamine.

4. The method of claim 1 wherein the compound is 4,5-dihydro-N-(1,2,3,4-tetrahydro-1-naphthalenyl)-2-oxazolamine.

5. The method of claim 1 wherein the compound is 4,5-dihydro-N-(1-phenylethyl)-2-oxazolamine.

* * * * *